United States Patent [19]

Daub

[11] Patent Number: 5,148,567
[45] Date of Patent: Sep. 22, 1992

[54] TOOTHBRUSH

[76] Inventor: Craig C. Daub, 5222 E. Bald Eagle Blvd., White Bear Lake, Minn. 55110

[21] Appl. No.: 750,101

[22] Filed: Aug. 26, 1991

[51] Int. Cl.⁵ .................. A61C 17/34; A46B 9/04; A46B 13/02
[52] U.S. Cl. ................................... 15/22.1; 15/167.2; 300/21
[58] Field of Search ............... 15/22.1, 22.2, 167.1, 15/167.2; 300/21

[56] References Cited

U.S. PATENT DOCUMENTS

| | | | |
|---|---|---|---|
| 4,493,125 | 1/1985 | Collis | 15/167.2 |
| 5,027,463 | 7/1991 | Daub | 15/22.1 |

FOREIGN PATENT DOCUMENTS 2449513  4/1976  Fed. Rep. of Germany ..... 15/167.2

*Primary Examiner*—Edward L. Roberts
*Attorney, Agent, or Firm*—Herman H. Bains

[57] ABSTRACT

An electric toothbrush permits simultaneously brushing and cleaning of the occlusal, lingual and buccal surfaces of the upper and lower teeth of a user. This includes a bristle support member which anchors a plurality of longitudinally extending central rows of bristle tufts that extend outwardly from opposite surfaces thereof. Each surface of the bristle support member has slots herein which receive elongate brush elements having arcuately bent bristles which define outer rows for engaging the lingual and buccal surfaces.

5 Claims, 1 Drawing Sheet

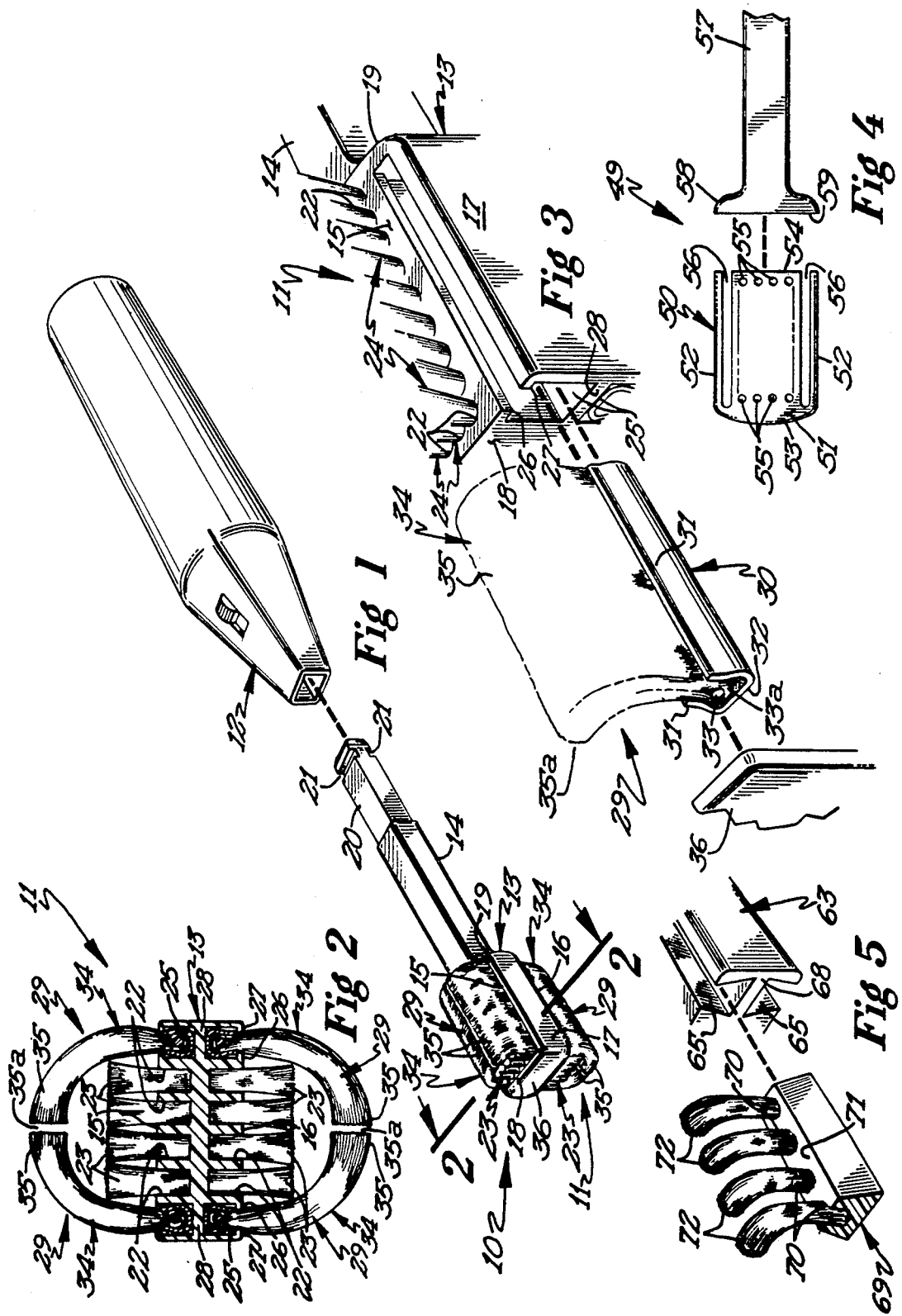

TOOTHBRUSH

FIELD OF THE INVENTION

This invention relates to toothbrushes and more particularly to an electric toothbrush which simultaneously brushes the users upper and lower teeth.

BACKGROUND OF THE INVENTION

This application is an improvement on my U.S. Pat. No. 5,027,463. Research data indicates that the average person spends less than one to three minutes brushing his or her teeth per day. On the other hand, dentists recommend that approximately three minutes of brushing three times per day is needed in order to maintain good oral hygiene. Apparently recognizing that the average person simply does not devote sufficient time in brushing his or her teeth, various designs in toothbrush construction have been developed to increase the cleaning efficiency for the individual but with limited success due to the human element involved.

Recommended brushing techniques have changed over the years. The fifties had the individual brushing up and down. Late sixties and seventies advocated the Bass technique of a circular motion. The mid eighties to present are now advocating a back and forth motion (reciprocating) to sweep the bristles below the gumline and break up the plaque. This reciprocating motion definitely has proved the most effective in the battle against periodontal disease and is supported by this toothbrush's reciprocating design.

It has been the endeavor to have all the qualities incorporated into this toothbrush. These qualities are a brush that is simple and easy to use, clinically effective with dramatic and immediate results, total plaque control, acceptable time expense, patient self-education, enjoyable and feels good, visual feedback, and sensory feedback from very smooth and clean teeth.

However, the human elements of handicaps, laziness, lack of knowledge in what is to be accomplished, lack of dexterity, amount of time spent brushing, and knowledge of proper and complete brushing skills has eluded both the user and the toothbrush industry. This is why 3 out of 4 adults have some form of periodontal disease (some experts say it is over 90%). Brushing alone is not enough, rather the complete removal of plaque is essential in the preservation of healthy teeth, gums, and supporting bone. Plaque is a soft, sticky, colorless film of bacteria constantly forming on our teeth. It combines with sugar and other carbohydrates to form acids, which attack tooth enamel and can cause cavities. Plaque can also cause inflammation of the gums (gingivitis), which can be identified by swollen, bleeding gums. If not treated early, gingivitis can lead to periodontitis, a more serious condition that causes gums to recede and bone to deteriorate. As a result, the supporting structures are weakened and teeth become loose. It is easy to see why thorough brushing to remove plaque is essential to keep teeth, gums, and bone healthy. We all know the importance of having the individuals remove plaque on a daily basis. We also recognize the difficulties associated with motivating them to comply with a consistent and conscientious home dental care regimen. The public needs a regimen that is easy to adopt and easy to follow.

U.S. Pat. No. 3,100,309 to Gambino discloses a toothbrush which has rows of curved bristles and a straight row of bristles. The rows of bristles extend transversely of the handle and presents a rather cumbersome arrangement.

U.S. Pat. No. 4,382,309, to Collis, discloses a toothbrush having two outer rows of curved bristle tufts and a single row of short, straight bristle tufts which are intended to simultaneously brush the lingual, buccal, and occlusal surfaces of the teeth.

The general design in the Collis Patent probably would increase the cleaning efficiency of the toothbrush compared to the conventional toothbrush head. However, the use of a single central row of bristle tufts for brushing the occlusal surfaces and the single outer rows of bristle tufts for brushing the lingual and buccal surfaces in the Collis toothbrush is ineffective in achieving good oral hygiene, especially if the user brushes for less than one minute.

SUMMARY OF THE INVENTION

It is an object of this invention to provide a novel and improved electric toothbrush which is completely effective during use to simultaneously brush the upper and lower teeth of the user plaque free.

More specifically, it is an object of this invention to provide a novel toothbrush for simultaneously brushing the buccal, lingual, and occlusal surfaces of the teeth for both the upper and lower arches. Because of its unique construction, a user of this novel toothbrush can achieve the equivalence of nine minutes of manual brushing in $1\frac{1}{2}$ minutes not taking into account the speed at which the electric reciprocating brush head runs at.

The average individual has the capability of generating manually between 160-200 brushing strokes per minute. This novel toothbrush will reciprocate brushing strokes between 800-1700 RPM's depending on the force with which the user closes down on the toothbrush. This represents anywhere from a 700% to 1000% increase in the number of brushing strokes delivered per minute when compared with manual brushing.

In the preferred embodiment, my novel toothbrush comprises an electric brush to facilitate brushing by a user. The toothbrush includes a flat bristle support member having opposed flat surfaces provided with openings therein for accommodating bundles of tufted bristles and slots for accommodating channel brushes or a tufted design. The interior rows of bristle bundles are straight, while the exterior rows of bristle bundles or channel bristles are bent or curved and serve to brush the lingual and buccal surfaces of the teeth. The bristled channels (outer rows) flex open to accommodate the wider molars and flex back in to clean the narrow anterior teeth. Because the brush head provides equal amounts of brushing to both arches as well as the occlusal, buccal, and lingual surfaces, there are no skipped areas due to human error. All of the rows of bristles are disposed in substantially parallel relation to the longitudinal edges of a bristle support member.

In the preferred embodiment, the bristles are preferably formed of polyester resin, (although any synthetic resin could theoretically be used) and the bristles are of uniform diameter. Since the flexibility (softness) and rigidity (stiffness) of the bristles of uniform diameter is a function of the bristle length, the exterior rows of bristles bundles, which are the longest, are the most flexible (softest). The shorter bristles of the four interior rows are the most rigid of the bristles and brush the occlusal surfaces of the teeth.

More specifically, it is an object of this invention to provide a novel electric toothbrush having an identical bristle arrangement on both brush surfaces of the toothbrush head including a plurality of central rows of bristle tufts and a pair of arcuately bent outer rows of bristles. The central rows of bristle tufts engage and brush the chewing (occlusal) surface of the teeth while the outer rows of bristles brush the outside (buccal) and inside (lingual) surfaces of the teeth.

The tufted bundles of bristles forming the central rows are applied to symmetrically arranged openings in the bristle support member of the toothbrush head in a conventional manner. However, each surface of the bristle support member of the toothbrush head is provided with a pair of elongate slots therein for accommodating the outer rows of bristles.

The outer rows of bristles are preformed and curved before insertion into the slots in the bristles support member. In preforming the outer rows of bristles, the bristles are inserted into a metal channel containing a binding wire. The binding wire is forced downwardly to cause the fill material to form vertically as the channel is closed over the looped portion of the bristles.

The bristles forming the outer rows are continuous (or tufted) and are set, end rounded, polished and then heat set to provide arcuate bending of the upper end portions of the bristles. The preformed rows of bristles are then inserted into the slots of the bristle support member and the upper ends of the outer row bristles overlie the upper ends of the bristles of the central rows. The construction of the electric toothbrush comprising the instant invention permits ease in manufacture while substantially retaining the features and advantages of the toothbrush disclosed in my U.S. Pat. No. 5,027,463.

FIGURES OF THE DRAWING

FIG. 1 is an exploded perspective view of the novel electric toothbrush;

FIG. 2 is a cross-sectional view of FIG. 1 and looking in the direction of the arrows;

FIG. 3 is a fragmentary perspective of a portion of the toothbrush illustrating details of construction thereof;

FIG. 4 is a modified form of the bristle support member and interconnecting member;

FIG. 5 illustrates the bristles in the outer rows as tufted rather than in a modified form of an outer brush element illustrating continuous rows.

DESCRIPTION OF THE PREFERRED EMBODIMENT

Referring now to the drawings and more specifically to FIGS. 1-3, it will be seen that one embodiment of my novel electric toothbrush, designated generally by the reference numeral 10 is thereshown. The toothbrush 10 includes a head 11 and a combination electric motor module and handle 12 detachably connected to the head. The head is comprised of a generally rectangular shaped flat bristle support member 13 and has an elongate interconnecting member 14 rigidly secured thereto and projecting therefrom. The bristle support member 13 includes an upper planar surface 15, a lower planar surface 16, opposed longitudinal side edges 17, a transverse front edge 18, and a transverse rear edge 19.

It will be seen that the outer end portion 20 of the interconnecting member 14 is of reduced cross-sectional size and is provided with locking notches 21 therein for coupling connection in a well known manner to the drive connection of the combination electric motor module and handle 12. This reduced end portion 20 is inserted into the socket in the electric motor module and handle 12. The electric motor module and handle may be battery operated as well as through a conventional AC transformer.

It will be noted that each of the planar upper and lower surfaces of the bristle support member 13 has a plurality of openings 22 therein which are arranged in longitudinal rows extending from the adjacent front transverse edge 18 to a point adjacent the rear transverse edge 19. These openings 22 accommodate ends of the bristles comprising the tufted bundles 23 so that each tufted bundle projects from the associated planar surface of the bristle support member. The bristles comprising each tufted bundle 23 are of the same diameter and are preferably formed of polyester resin. Each bristle has a diameter of approximately 0.006-0.007 inches. Unlike the nylon bristles of most conventional toothbrushes, the polyester bristles of the present toothbrush are not noticeably affected by water absorption and therefore do not develop the soft effects caused by water absorption. It will be noted that in the preferred embodiment, there are four longitudinal rows of bristle bundles projecting from each upper and lower planar surface of the bristle support member 13. Although three rows or possibly five rows of bristles may be used, it has been found that four rows produce the optimal brushing effect for the occlusal or chewing surface of an average user's teeth.

The upper planar surface 15 and the lower planar surface 16 of the bristle support member are each provided with a pair of longitudinally extending elongate slots 25 therein as best seen in FIG. 3. It will be noted that each slot 25 in each planar surface is located adjacent each longitudinal side edge 17 and extends from a point adjacent each transverse rear edge 19 through the transverse front edge 18. Referring now to FIG. 3, it will be noted that each slot 25 is enlarged at a location below the adjacent planar surface to define an outwardly projecting elongate lip 26 and an inwardly projecting elongate lip 27. It will further be noted that a septum 28 is defined between a slot in one planar surface and the adjacent slot in the other planar surface. A slot in one planar surface is vertically aligned with a slot in the other planar surface.

Each of the slots 25 accommodates an elongate outer brush element 29 which is preformed prior to insertion into the associated slot. Each of these outer brush elements 29 includes an elongate channel 30 formed of stainless steel, aluminum or the like, and including legs 31 interconnected by base portion 32. The channel 30 has a fill material 33a positioned therein and a binding wire 33 positioned over the fill material. The binding wire 33 is of round cross-sectional configuration and is preferably formed from stainless steel. The fill material may include nylon, polypropylene, polyethelene, polyvinyl cloride, polystyrene or polyester. The lower portions of a continuous row of bristles 34 extend into and are secured by the channel 30 and the binding wire 33.

During the formation of the outer brush element 29, the binding wire is forced downward into the fill material which causes the fill to form vertically at the same time the channel forming strip is shaped into a channel to close over the wire and the looped portion of the fill material thus forming the bristles. The length of the brush element 29 will correspond to the length of the slot 25 into which it will be inserted. However, the upper end portions of the continuous row of bristles 34 are first end-rounded, polished, and then heated and arcuately bent to the shape illustrated in FIG. 1. In this regard, when each brush element 29 is inserted into one of the slots 25, the upwardly or outwardly curved ends 35 adjacent one longitudinal side edge 17 will extend inwardly towards the inwardly curved ends 35 of the bristle row of the brush element 29 positioned in the other slot 25 as shown in FIG. 2.

It will be noted that the inwardly curved end portions 35 of each pair of brush elements 29 have their ends 35a positioned in opposed but spaced apart relation. It will also be noted that these inwardly curved ends 35 for the brush elements on one surface of the bristle support member overlie the upper ends of the interior rows of bristles. The bristles of the outer rows may be arranged as a continuous row, as illustrated in FIG. 1 to 3, or the bristles may be arranged in tufts as shown in FIG. 5.

After the outer brush elements 29 have been inserted into the associated slots 25, these brush elements are secured in place by a rectangular shaped retaining bar 36 which is formed of the same plastic or nylon material as the bristle support member 13. The retaining bar 36 is rigidly secured to the transverse front edge 18 by a suitable cement, glue, or ultrasonic weld which completes the assembly of the head 11.

Referring now to FIG. 4, it will be seen that a different embodiment of the toothbrush head, designated generally by the reference numeral 49 is thereshown. The head 49 also includes a generally rectangular shaped bristle support member 50 having a planar upper surface 51, a planar lower surface (not shown), longitudinal side edges 52, a transverse front edge 53, and a transverse rear edge 54. The bristle support member 50 also has a plurality of openings 55 in the upper and lower planar surfaces thereof in the manner of the embodiment of FIG. 1. These openings are also arranged in longitudinally extending rows and each accommodates a tuft of bristles therein in the manner of the embodiment of FIG. 1.

Each planar surface of the bristle support member also has a pair of elongate slots 56 therein, each slot being positioned adjacent one of the longitudinal side edges 52. However, in the embodiment of FIG. 4, each slot extends from adjacent the transverse front edge 53 through the transverse rear edge 54. Otherwise, the slots in the bristle support member 50 are identical to those in FIG. 1. The interconnecting member 57 is of elongate configuration and is produced as a separate component with respect to the bristle support head. Otherwise, the interconnecting member 57 is of similar if not identical construction to that illustrated in the embodiment of FIG. 1.

It will be noted that the interconnecting member 57 has an enlarged end 58 having a substantially planar front edge 59. When the brush elements are inserted into the slots of 56, the final assembly of the head 49 requires the attachment of the interconnecting member 57 to the bristle support member. The transverse front edge 59 is rigidly secured to the transverse rear edge 54 of the bristle support member by a suitable cement, glue, ultrasonic weld or the like to thereby lock the brush elements into the slots 56. In this regard, the transverse front edge 59 corresponds in its transverse (width) dimension to the transverse dimension of the transverse rear edge 54.

In use, the interior rows 24 (FIG. 3) of the tufted bristle bundles 23 (FIG. 2) engage the occlusal surfaces of the user's upper and lower teeth during the brushing operation. The upper surface of the tufted bundles 23 of the interior rows 24 are disposed substantially in a transverse plane and are sufficient (preferably 4 rows) to completely brush the occlusal surface plaque free during the brushing operation.

The brush elements 29 which project out from each planar surface of the bristle support member actually constitute the outer rows for the toothbrush head. The outer rows of bristles are highly effective in brushing the buccal and lingual surfaces of the user's teeth plaque free during the brushing operation.

Referring again to FIG. 5, it will be noted that the bristle support member 63 is provided with slots 65 therein which correspond to the slots 25 in the bristle support member 13. However, the slots 65 are somewhat different in configuration than the slots 25 but the bristle support member 63 is otherwise identical to the bristle support member 13. It will be seen that the slots 65 are of dovetail configuration and planes outwardly and downwardly to the septum 68.

Each slot 65 receive an elongate outer brush element 69 having a trapezoidal configuration for sliding engagement in a slot 65. The upper or outer surface 71 of each brush element 69 has a plurality of longitudinally spaced apart openings 70 therein each accommodating a tufted bristle bundle 72 therein. The bristles comprising the bundles are preferably identical to the bristles 34 of the embodiment of FIG. 1. The outer ends of the bristles are curved inwardly in the manner of the bristles 34. The brush element 69 is preferably formed of a plastic material and provides the same advantages as the brush element 29 of the embodiment of FIG. 1.

It will be seen that my novel toothbrush permits simultaneous brushing and cleaning of a user's upper and lower teeth.

It will also be seen that my novel and improved toothbrush is arranged and constructed to permit ease in manufacture thereof.

What is claimed is:

1. A toothbrush comprising,
   an elongate head including a rectangular shaped bristle support member, an elongate connecting member secured to said bristle support member and projecting therefrom, a combination electric motor and handle module having a socket therein, said connecting member projecting into said socket and being operatively connected to the electric motor and handle module whereby when said electric motor is energized, said head will be reciprocated,
   said bristle support member having opposed substantially planar surfaces, a front transverse edge, a rear transverse edge, and opposed longitudinal edges, each planar surface having a pair of elongate longitudinally extending slots therein, each slot in said planar surface extending from a point adjacent one transverse edge through the other transverse edge thereof,
   a plurality of elongate bristles arranged in tufted bristle bundles secured to said opposed planar surfaces and extending outwardly therefrom, said tufted bristle bundles being arranged in parallel, spaced apart longitudinally extending interior rows on each planar surface located inwardly of the parallel slots in the associated planar surface,
   a plurality of outer brush elements each including an elongate rigid channel having, a plurality of elongate bristles therein defining an outer row of bristles, the outer ends of the outer row of bristles being arcuately bent, said channel of each brush element being positioned in one of said slots so that the bristles thereof project outwardly of the associated planar surface, means secured to said other transverse edge of the bristle support member for retaining said brush elements in said slots, outer ends of the bristles of each brush element extending over the interior rows of bristles whereby a user can simultaneously brush the occlusal, lingual and buccal surfaces of both the upper and lower arch of the user's teeth.

2. The toothbrush as defined in claim 1 wherein said slots in said bristle support member extend through the front transverse edge of the bristle support member, said retaining means being secured to said front transverse edge to obstruct the slots in the bristle support member.

3. The toothbrush as defined in claim 1 wherein said slots in said bristle support member extend through the rear transverse edge thereof, said connecting member comprising retaining means and having one end thereof secured to said rear transverse edge in obstructing relation to said slots.

4. The toothbrush as defined in claim 1 wherein the bristles of each said outer brush elements are arranged to define a continuous row of bristles.

5. The toothbrush as defined in claim 1 wherein the bristle of the outer brush elements are arranged in tufted bristle bundles.

* * * * *